(12) United States Patent
Bonfante, Jr.

(10) Patent No.: US 10,822,013 B2
(45) Date of Patent: Nov. 3, 2020

(54) MOTOR VEHICLE HAND CONTROL FOR DIFFERENTLY ABLED INDIVIDUALS

(71) Applicant: Mario Bonfante, Jr., Laguna Hills, CA (US)

(72) Inventor: Mario Bonfante, Jr., Laguna Hills, CA (US)

( * ) Notice: Subject to any disclaimer, the term of this patent is extended or adjusted under 35 U.S.C. 154(b) by 84 days.

(21) Appl. No.: 15/523,010

(22) PCT Filed: Oct. 30, 2015

(86) PCT No.: PCT/US2015/058301
§ 371 (c)(1),
(2) Date: Apr. 28, 2017

(87) PCT Pub. No.: WO2016/070035
PCT Pub. Date: May 6, 2016

(65) Prior Publication Data
US 2017/0355390 A1    Dec. 14, 2017

Related U.S. Application Data

(60) Provisional application No. 62/073,338, filed on Oct. 31, 2014.

(51) Int. Cl.
| | |
|---|---|
| *B62D 1/04* | (2006.01) |
| *F16H 59/04* | (2006.01) |
| *B60T 7/10* | (2006.01) |
| *B60K 23/02* | (2006.01) |
| *B60K 20/06* | (2006.01) |
| *B62D 1/14* | (2006.01) |
| *A61F 4/00* | (2006.01) |

(Continued)

(52) U.S. Cl.
CPC ............... *B62D 1/04* (2013.01); *A61F 4/00* (2013.01); *B60K 20/06* (2013.01); *B60K 23/02* (2013.01); *B60T 7/10* (2013.01); *B62D 1/046* (2013.01); *B62D 1/14* (2013.01); *B62D 15/0215* (2013.01); *F16H 59/044* (2013.01); *B60W 30/00* (2013.01); *B60Y 2400/83* (2013.01)

(58) Field of Classification Search
CPC .. B62D 1/046; B62D 1/14; G05G 1/04; F02D 9/08; B60K 23/02; B60K 2741/003; B60T 7/10; F16H 59/044
See application file for complete search history.

(56) References Cited

U.S. PATENT DOCUMENTS

| | | | | |
|---|---|---|---|---|
| 2,471,244 A | * | 5/1949 | Self .......................... | B60T 7/08 180/78 |
| 2,997,147 A | * | 8/1961 | Bilz ........................ | F16H 37/00 192/226 |

(Continued)

OTHER PUBLICATIONS

"Mario Bonfante's Custom Hand Controls/KripTrol Build Video" uploaded by Mario Bonfante, Jul. 3, 2013, https://www.youtube.com/watch?v=o6DyB7v-aRo&app=desktop.*

(Continued)

*Primary Examiner* — Drew J Brown
(74) *Attorney, Agent, or Firm* — Carlson, Gaskey & Olds, P.C.

(57) ABSTRACT

A disclosed vehicle control system provides control over complex vehicle functions including transmission shifting to enable differently abled drivers to operate a motor vehicle.

11 Claims, 6 Drawing Sheets

(51) Int. Cl.
  *B62D 15/02*   (2006.01)
  *B60W 30/00*   (2006.01)

(56) References Cited

U.S. PATENT DOCUMENTS

| | | | | |
|---|---|---|---|---|
| 3,117,649 | A * | 1/1964 | Parton | B60W 10/06 |
| | | | | 180/333 |
| 3,856,123 | A * | 12/1974 | Kinsey | B62M 25/04 |
| | | | | 192/3.62 |
| 3,896,680 | A * | 7/1975 | Shoemaker | B62K 23/04 |
| | | | | 192/89.21 |
| 4,580,652 | A * | 4/1986 | Turner | A61G 3/061 |
| | | | | 180/11 |
| 4,826,391 | A * | 5/1989 | Lawrence | B25J 13/088 |
| | | | | 414/688 |
| 5,335,743 | A * | 8/1994 | Gillbrand | B60K 20/02 |
| | | | | 180/170 |
| 5,666,857 | A * | 9/1997 | Sebazco | B60T 7/02 |
| | | | | 180/333 |
| 7,775,884 | B1 * | 8/2010 | McCauley | A63F 13/06 |
| | | | | 463/39 |
| 8,151,666 | B1 * | 4/2012 | Kraus | G05G 11/00 |
| | | | | 74/488 |
| 2003/0160412 | A1 * | 8/2003 | Constans | B60T 7/10 |
| | | | | 280/88 |
| 2005/0067889 | A1 * | 3/2005 | Chernoff | B60T 7/10 |
| | | | | 303/20 |
| 2009/0309346 | A1 * | 12/2009 | Van Druff | B60R 22/26 |
| | | | | 280/806 |
| 2010/0056331 | A1 * | 3/2010 | Johansson | B60K 20/04 |
| | | | | 477/92 |
| 2016/0052390 | A1 * | 2/2016 | Park | B60K 26/02 |
| | | | | 74/473.31 |

OTHER PUBLICATIONS

"Mario Bonfantes 1st Test Drive with the KripTrol (Handcontrols)" uploaded by Mario Bonfante, Jul. 15, 2013, https://www.youtube.com/watch?v=cT1cv6fUC9M.*

"Mario Bonfante's KripTolled BMW M3 1st time on track!" uploaded by Mario Bonfante, Aug. 19, 2013, https://www.youtube.com/watch?v=HPMPrWVhY7U.*

* cited by examiner

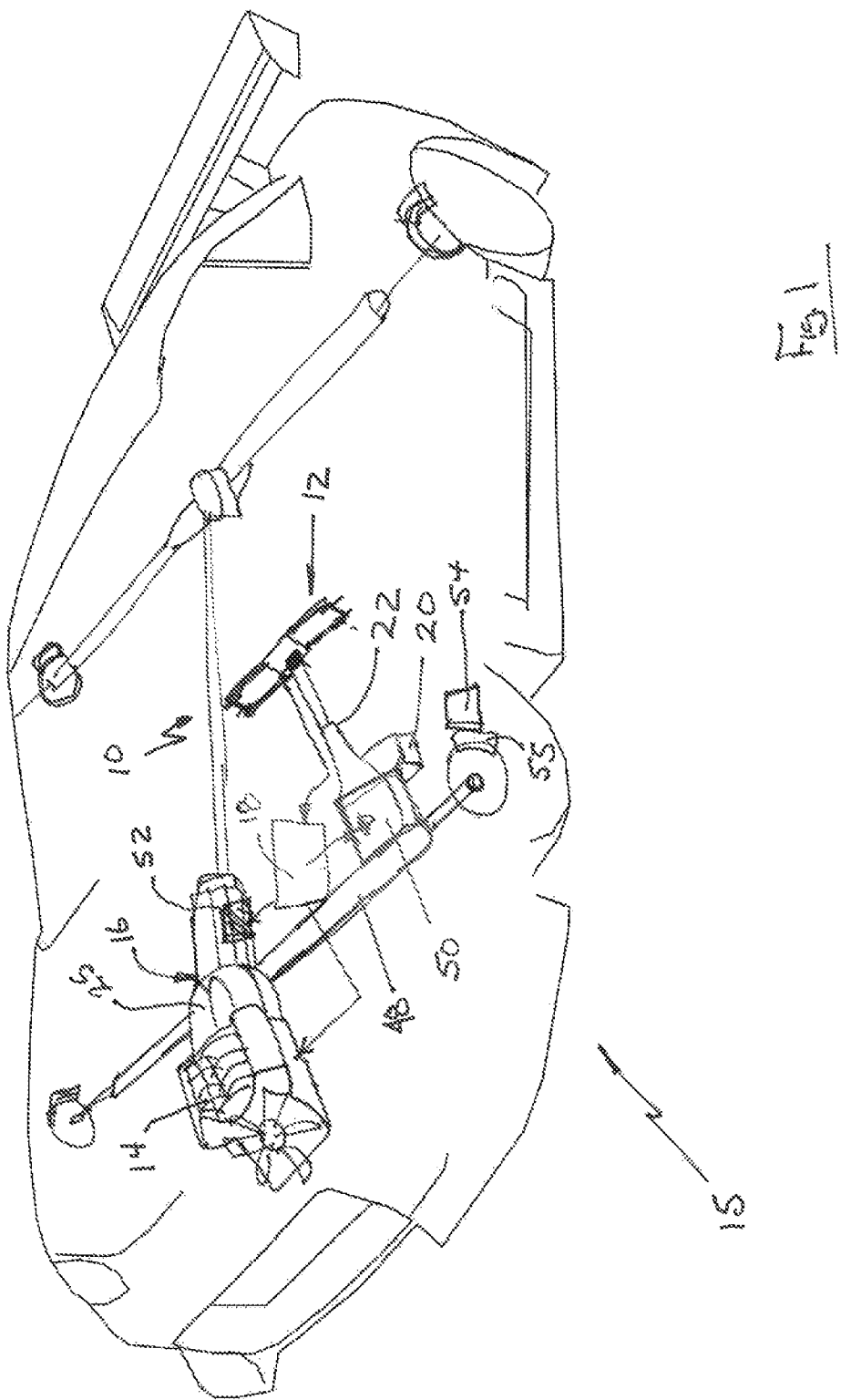

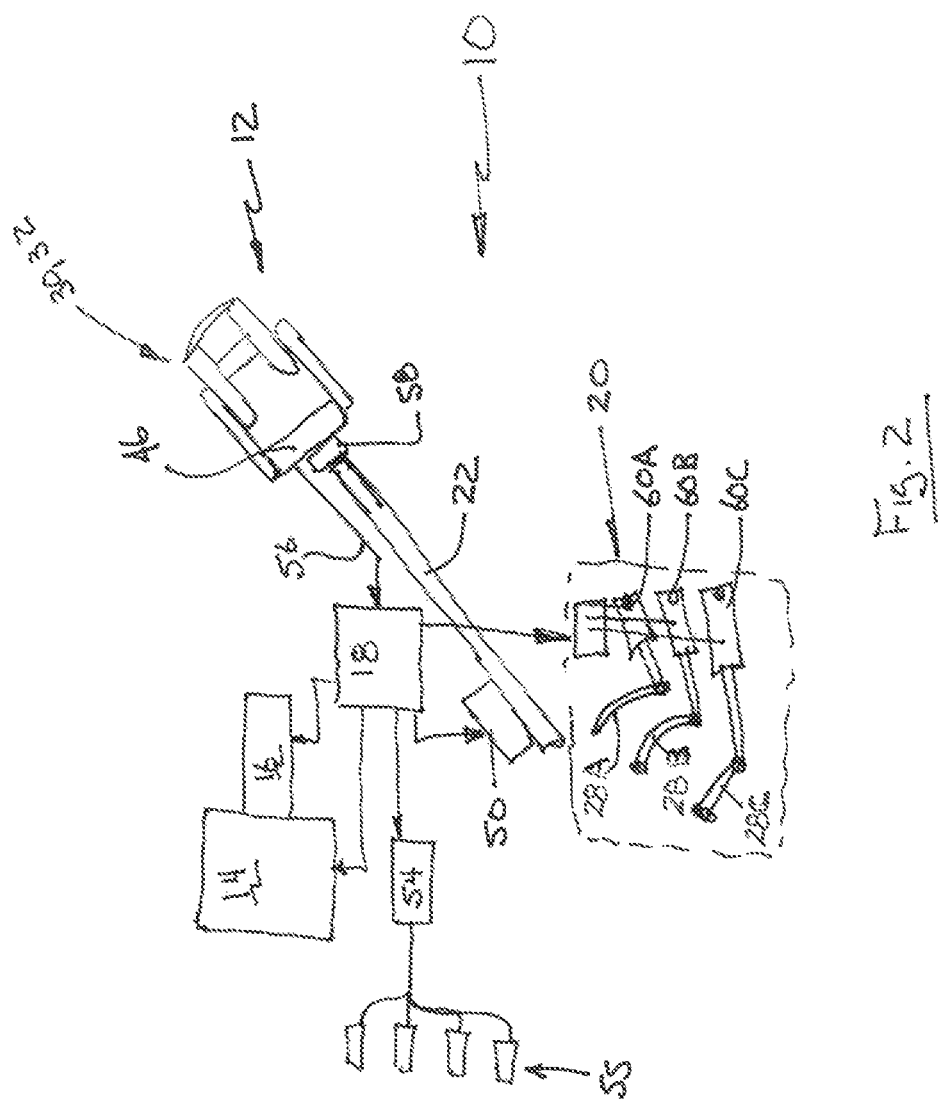

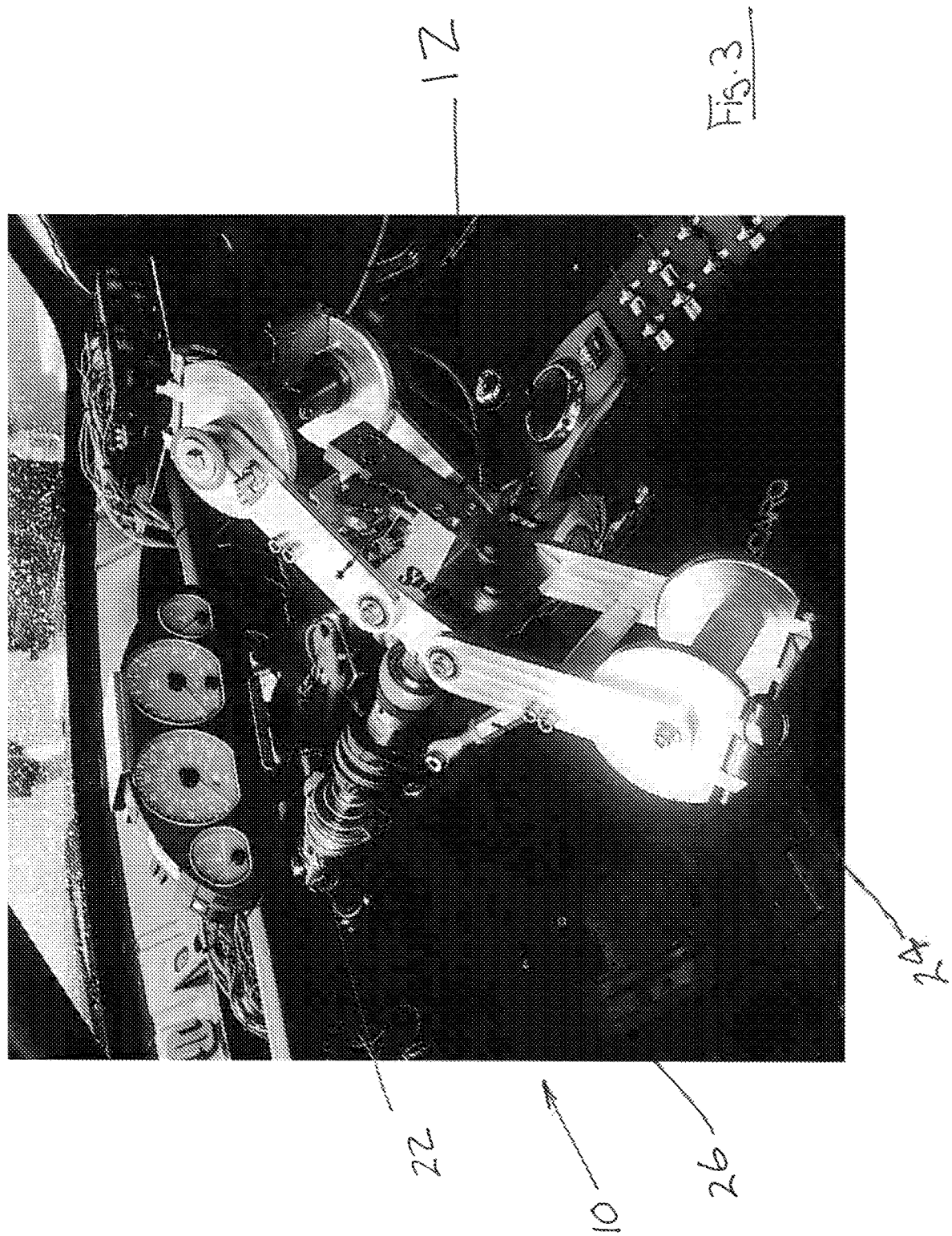

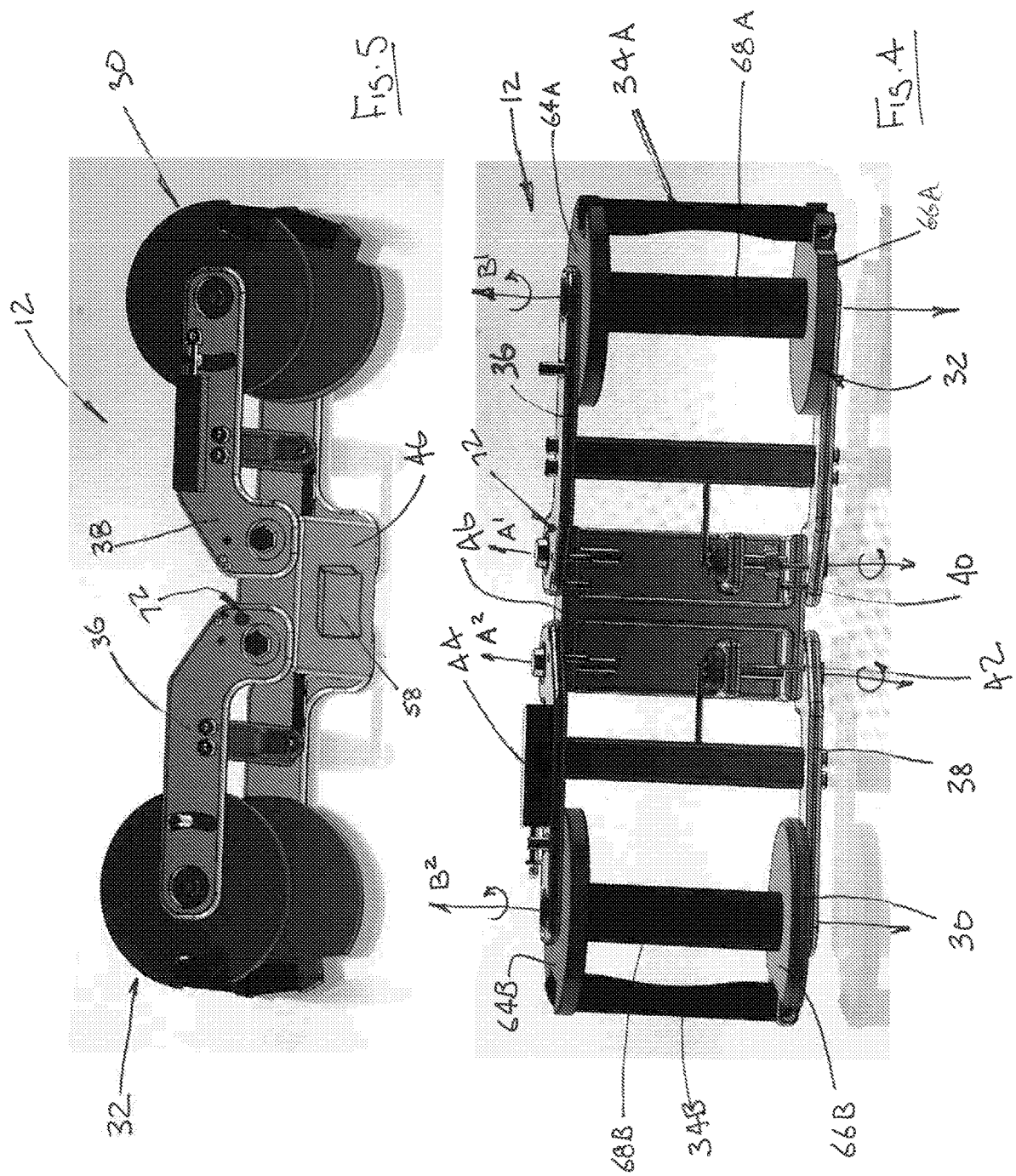

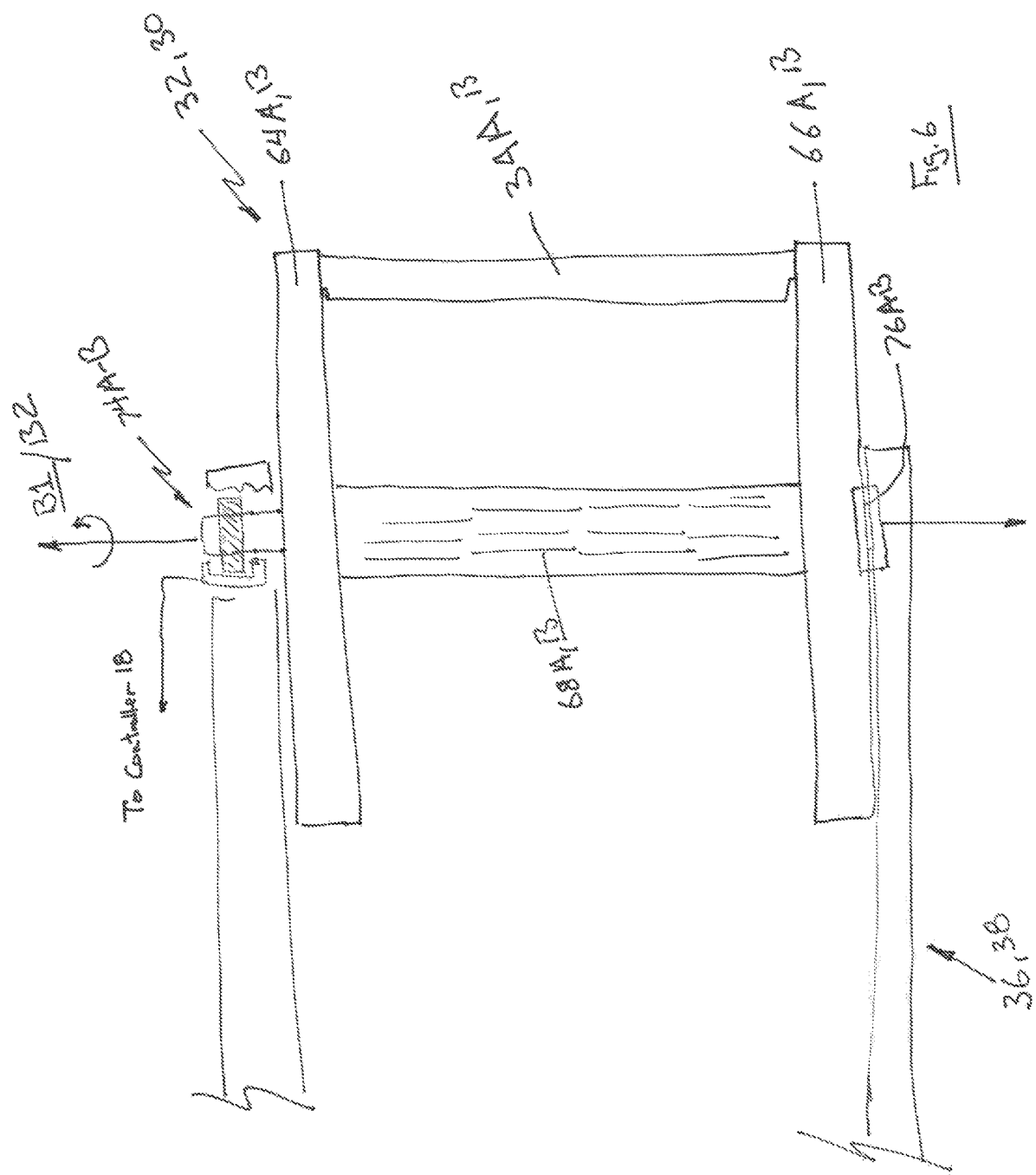

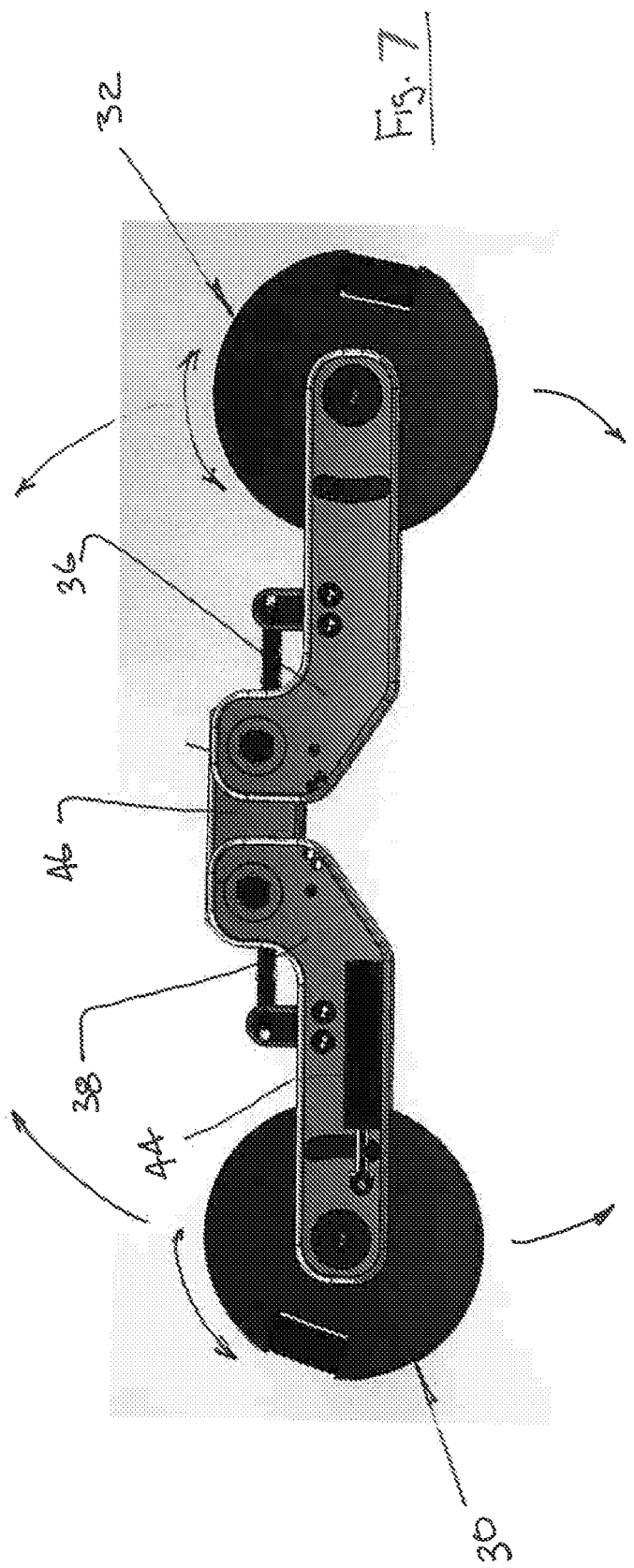

MOTOR VEHICLE HAND CONTROL FOR DIFFERENTLY ABLED INDIVIDUALS

CROSS REFERENCE TO RELATED APPLICATION

This application claims priority to U.S. Provisional Application No. 62/073,338 filed Oct. 31, 2014.

BACKGROUND

A disclosed driving system is incorporated into a motor vehicle to enable differently abled individuals to operate a motor vehicle.

Individuals that have experienced a life-altering injury and that have limited mobility and use of hands, arms and other extremities have been unfortunately excluded from operating motor vehicles due to the level of dexterity and the physical demands of driving.

SUMMARY

A disclosed vehicle control system provides control over complex vehicle functions including transmission shifting to enable differently abled drivers to operate a motor vehicle.

An exemplary embodiment of a vehicle control system according to this disclosure, among other possible things includes a base portion mountable to a steering column, a first arm portion pivotally mounted to the base and a second arm pivotally mounted to the base. A first spool rotatably mounted to the first arm and rotatable to actuate a vehicle throttle function and a second spool mounted to the second arm and rotatable to actuate a clutch function of the vehicle. The first arm is movable for applying a brake of a motor vehicle, and the second arm is movable for actuating gear changes of the motor vehicle.

Although the different examples have the specific components shown in the illustrations, embodiments of this disclosure are not limited to those particular combinations. It is possible to use some of the components or features from one of the examples in combination with features or components from another one of the examples.

These and other features disclosed herein can be best understood from the following specification and drawings, the following of which is a brief description.

BRIEF DESCRIPTION OF THE DRAWINGS

FIG. 1 is a schematic view of an example vehicle including a hand control assembly.

FIG. 2 is a schematic representation of the example system for controlling a vehicle for a differently abled individual.

FIG. 3 is perspective view of an example hand controlled device for a differently abled individual.

FIG. 4 is a front view of the example hand control device.

FIG. 5 is a top view of the example hand control device.

FIG. 6 is a side view of an example spool of the disclosed hand control device.

FIG. 7 is another top view of the example hand control device.

DESCRIPTION

Referring to FIG. 1, an example vehicle 15 is schematically shown and includes a motor 14, transmission 16, brake system 55 and control system 10. The control system 10 includes a hand control device 12 mounted where a standard steering wheel is typically mounted on a steering column 22 of the vehicle 15. The example hand control device 12 provides a means to control all vehicle functions by an operator with limited dexterity and mobility. It should be appreciated that the example hand control device 12 may be utilized to operate any type of vehicle, and/or driving simulator or game where control over common driving functions is required.

Accordingly, the example control device 12 provides throttle control, brake control as well as clutch actuation and gear shifting capability tailored operation by a differently abled vehicle operator. In this example, the hand control device 12 is part of a system 10 integrated into a vehicle to enable control of all vehicle functions with only limited movement of an operators hands and arms.

Referring to FIG. 2 with continued reference to FIG. 1, the example hand control device 12 includes features that communicate with a controller 18 to control operation of the motor 14 and transmission 16. The example controller 18 could be a separate dedicated controller for the hand control device 12, or could be implanted as a software program in an existing vehicle Electronic Control Unit (ECU). Moreover, the hand control unit 12 could include specific connections to enable use with an existing vehicle ECU. The hand control device 12 further includes features that communicate with a pedal box 20 utilized to control operation of conventional vehicle pedals 28A-C. The example pedal box 20 includes actuators 60A-C that are actuated by the controller 18 responsive to command signals 56 generated by the hand control device 12. The actuators 60A-C could operate hydraulically, electrically, pneumatically or by way of any other operating means responsive to signals generated by the hand control device 12. As appreciated, the control functions of the throttle, brake and clutch could be operated entirely by signals generated through control movements of the hand control device 12 and therefore not require the pedal box 20.

Referring to FIG. 3, one disclosed example embodiment includes controls implemented by manual operation of the hand control device 12. One illustrated example is mechanical control of vehicle braking system 54 through a mechanical linkage between a portion of the vehicle control 12 and an existing brake pedal 28 in the vehicle. In this example, a first link 24 is attached to a second link 26. The second link 26 is movable along the steering column 22 to enable rotation of the hand control 12 while also allowing movement axially along the steering column 22. The second link 26 is in turn attached either directly or through another link to the brake pedal to control braking in response to actuation of the hand control 12. In this manner, the hand control 12 can be utilized and adapted for use in vehicles that include conventional controls.

Referring to FIGS. 4, 5, 6 and 7 with continued reference to FIG. 2, the disclosed hand control 12 includes a first arm 36 and a second arm 38 that are each pivotally mounted to a base portion 46. The first arm 36 includes an upper portion and lower portion that extend from the base portion 46 and pivot together about Axis A1. The second arm 38 includes an upper portion and a lower portion that pivot together about an Axis A2. The base portion 46 is mountable to the steering column 22 of the vehicle. In one example embodiment, the base portion 46 is mounted to the steering column 22 such that the steering column rotates responsive to rotation of the hand control 12. In another disclosed embodiment, the base portion 46 rotates to drive a steering sensor 58 (schematically shown in FIG. 5) that generates a signal that is processed by the controller 18 to provide a signal to an actuator 50 of the steering system 48 that commands a proportional turn of the wheels. The steering sensor 58 may be any sensor capable of generating signals indicative of a rotation of the hand control 12.

The upper and lower portions of the first arm spaced apart to support a first spool 32 therebetween. The second arm 38 supports a second spool 30 between the upper and lower arms. The first spool 32 is rotatable about an axis B1 on the arm 36 and is utilized to control throttle functions of the vehicle 15. The second spool 30 is rotatable about an axis B2. The first and second spools 32, 30 provide the location for the operator's hands to operate the various control functions of the hand control 12.

Each of the first spool 32 and the second spool 32 include an upper flange 64A-B and a lower flange 66A-B attached to a gripping member 68A-B. The gripping member 68A-B is disposed along corresponding axes B1 and B2. A keeper bar 34A-B is attached at an outer periphery of the upper and lower flanges 64A-B, 66A-B for each spool 30, 32. The keeper bar 34A-B aids in maintaining the operator's hands on the spools 30, 32 during operation. The keeper bar 34A-B can be modified to accommodate the abilities of the operator to enable continuous engagement of the hand control 12 during operation.

Both the first arm 36 and the second arm 38 are movable relative to the base 46. In this example, the first arm 36 is movable about the axis A1 forward and back to shift gears of the transmission 16. In this example, the arm 36 is incremented forward to downshift and pulled back to upshift the transmission 16. In this example embodiment, the transmission 16 is a sequential transmission and therefore the first arm 36 is moved pulled back to upshift and pushed forward to downshift and returns to a beginning position after each shift. Subsequent movement forward or backward of the first arm 36 provides a corresponding upshift or downshift from the current gear.

Forward and backward movement of the first arm 36 is sensed by shift sensor assembly 40. The shift sensor 40 generates a signal that the controller 18 translates into a command to the transmission actuator 52 to shift the transmission 16. In the disclosed example the shift sensor assembly 40 is a micro-switch; however any sensor or switch that generates a signal responsive to movement of the first arm 36 could also be utilized and is within the contemplation of this disclosure. The first arm 36 is held in place by a ball spring detent 72 to prevent accidental shifts.

In this example, the first spool 32 supported on the first arm 36 provides the throttle function. The spool 32 twists relative to the arm 36 and operates as an accelerator similar to those utilized in motorcycles. The spool 32 includes a spring 76A (schematically shown in FIG. 6) that returns the spool to a neutral position. A throttle sensor 74A is provided that generates a signal sent to the controller 18 indicative of rotation to actuate the throttle and increase engine speed.

The second arm 38 provides a braking function. Pushing forward on the second arm 38 initiates actuation of the brake system 55 of the vehicle (Shown schematically in FIGS. 1 and 2). A brake sensor 42 senses movement of the second arm 38 and generates a signal indicative of that movement. A brake controller 54 then generates a signal corresponding movement of the second arm 38 to actuate individual brakes at each wheel. This movement is then relayed to the controller 18 and utilized either to directly control vehicle brakes through an electrically operated braking system or alternatively for communicating with a pedal box 20 that is mounted in the vehicle and operates the conventionally configured vehicle pedals, schematically indicated at 28 in FIG. 2.

The second spool 30 is rotatable to engage or disengage a vehicle clutch 25 (schematically shown in FIG. 1). The second spool 30 is configured like the first spool and includes a rotation sensor 74B and return spring 76B. In this example, the rotation sensor 74B generates a signal used to control the vehicle clutch 25.

A clutch lock 44 is disposed on the second arm 38. The spool 30 is rotatable to operate the vehicle clutch at lower speeds and the clutch lock 44 is configured to engage at a set vehicle speed. In the disclosed example once the vehicle accelerates past 3-5 miles per hour, the clutch lock 44 will lock the second spool 30 in place and prevent further actuation of the clutch 25. The example transmission 16 is a sequential transmission and therefore shifting occurs sequentially through upshifts and downshifts. Other types of transmission such as for example, an automatically shifted transmission or any other transmission configuration utilized with a motor vehicle are within the contemplation and are compatible with the disclosed hand control device 12.

Referring to FIG. 2 with continued reference to FIGS. 4, 5, 6 and 7, the example hand control 12 communicates electronically through the controller 18 with the pedal box 20. The pedal box 20 includes actuators 60A-C controlled by the controller 18 responsive to movements and signals 56 generated by the sensors provided in the hand control 12. The pedal box 20 may be retrofitted to control conventional pedals as is schematically illustrated. The pedal box 20 is mountable to a vehicle floor proximate to the pedals and interfaces with the current vehicle pedals 28 such that they are depressed or released depending on movement and signals generated by the hand control 12. Accordingly, in this way the hand control 12 can be adapted for implementation in any vehicle without significant modification to existing vehicle controls.

Accordingly, the example steering and vehicle control system provides control over complex vehicle functions including transmission shifting and control to enable limited mobility drivers with the opportunity to operate a motor vehicle.

Moreover, the example control device 12 may be utilized independent of a motor vehicle such as within a driving simulation device and/or gaming system. The control device 12 could be utilized to provide control functions for operation of a simulated driving experience for recreation and/or to provide an environment in which an operator could practice operation of the hand control device 12 independent of a motor vehicle. In such a system the control device 12 would be configured to provide inputs to the system generating a graphical representation of a vehicle. The inputs would be in the form of signals corresponding to operation of the graphical representation of the vehicle. Accordingly, for use with a driving simulation device, the example hand control device would be configured to provide inputs to the driving simulator for generating corresponding vehicle operation within a graphical representation generated by the driving simulator The terms forward and back are used in this disclosure are used to provide context for relative movement of features of the control device 12. In this disclosure the term forward is intended to mean vehicle forward and the term rearward is meant to mean vehicle rearward. Moreover, any additional directional terms relate to a position of a vehicle operator seated within a vehicle with a driver's position being on a left side of the vehicle. These directional descriptions are to clarify the features in this disclosure and not intended to be limited. Additionally, the term motor vehicle is utilized in this application to include vehicles such as go-carts, trucks, vans and automobiles including internal combustion engines, electric motors or any other known energy conversion device. One skilled in the art with the benefit of this disclosure will understand that different reference orientations are within the contemplation of this disclosure. Additionally, any term set out in this disclosure is provided as an example and could be structured differently to include making features integral or separating structures in to multiple components and still fall within the contemplation of this disclosure.

Although a preferred embodiment of this invention has been disclosed, a worker of ordinary skill in this art would recognize that certain modifications would come within the scope of this invention. For that reason, the following claims should be studied to determine the true scope and content of this invention.

What is claimed is:

1. A vehicle control system comprising:
   a base portion mountable to a steering column, the base portion movable to provide a steering input to the vehicle;
   a first arm portion pivotally mounted to the base and movable about a first axis, the first arm portion movable for actuating a gear change of a vehicle transmission;
   a second arm portion pivotally mounted to the base and movable about a second axis separate and independent of the first arm portion, the second arm portion movable for actuating a vehicle brake system;
   a first spool rotatably mounted to the first arm portion and rotatable about a first spool axis that is parallel to the first axis, the first spool rotatable to actuate a vehicle throttle function;
   a first rotation sensor generating a signal indicative of a rotational position of the first spool;
   a second spool mounted to the second arm portion and rotatable about a second spool axis that is parallel to the second axis, the second spool rotatable to actuate a clutch function of the vehicle;
   a second rotation sensor generating a signal indicative of a rotational position of the second spool;
   a detent maintaining a position of the second arm relative to the base to maintain a desired gear selection;
   a first position sensor generating a signal indicative of a position of the first arm relative to the base; and
   a second position sensor generating a signal indicative of a position of the second arm relative to the base, wherein the first position sensor sends a signal to a transmission controller to control shifting between gear ratios of a transmission, and the second position sensor sends signals to a brake controller for actuating the vehicle brakes.

2. The vehicle control system as recited in claim 1, wherein the first spool and the second spool comprise a top flange spaced apart from a bottom flange and connected by a gripping member.

3. The vehicle control system as recited in claim 2, wherein the first spool and the second spool are each rotatable about an axis extending longitudinally through the corresponding gripping member.

4. The vehicle control system as recited in claim 2, including a keep bar attached on one end to the top flange and on a second end to the bottom flange.

5. The vehicle control system as recited in claim 1, wherein the base portion is mounted for rotation relative to the steering column and includes a steering sensor measuring rotation of the base relative to the steering column.

6. The vehicle control system as recited in claim 5, including an actuator for operating a vehicle steering system responsive to the measured rotation by the steering sensor.

7. The vehicle control system as recited in claim 1, including a clutch lock supported proximate to the second spool for locking the second spool in a desired position to maintain the second spool in a position corresponding to engagement of a vehicle clutch.

8. The vehicle control system as recited in claim 1, including a link attached to the first arm portion for actuating the vehicle brake system responsive to movement of the first arm.

9. A control system for controlling vehicle functions comprising:
   a first arm portion movable by a vehicle operator for selecting a desired gear setting of a transmission;
   a second arm portion movable for applying a brake system, wherein the first arm portion and the second arm portion are independently moveable about separate first and second axes of rotation;
   a first spool mounted to the first arm portion and rotatable to actuate a vehicle accelerator;
   a second spool mounted to the second arm and to actuate a desired vehicle function, wherein the first spool and the second spool are rotatable about respective axes that are parallel to the separate axes of the first arm portion and the second arm portion;
   a first rotation sensor generating a signal indicative of a rotational position of the first spool;
   a second rotation sensor generating a signal indicative of a rotational position of the second spool; and
   a steering sensor generating a signal indicative of rotation of the base for actuating a vehicle steering system,
   wherein the first arm portion and the second arm portion are attached to a base and the base is rotatable responsive to rotational input into either of the first arm portion and the second arm portion.

10. The control system as recited in claim 9, wherein the first position sensor sends a signal to a transmission controller to control shifting between gear ratios of the transmission, and the second position sensor sends signals to a brake controller for actuating the vehicle brakes.

11. The control system as recited in claim 9, wherein the control system is configured to provide inputs to a system generating a graphical representation of a vehicle, the control system generating signals corresponding to operation of the graphical representation of the vehicle.

* * * * *